(12) United States Patent
Kraemer et al.

(10) Patent No.: US 9,931,064 B2
(45) Date of Patent: *Apr. 3, 2018

(54) MEASUREMENT SYSTEM FOR AN ANALYTE DETERMINATION AND A METHOD

(71) Applicant: Roche Diabetes Care, Inc., Indianapolis, IN (US)

(72) Inventors: Uwe Kraemer, Ilvesheim (DE); Juergen Rasch-Menges, Schwetzingen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/018,172

(22) Filed: Feb. 8, 2016

(65) Prior Publication Data

US 2016/0151001 A1 Jun. 2, 2016

Related U.S. Application Data

(63) Continuation of application No. 13/094,141, filed on Apr. 26, 2011, now Pat. No. 9,282,921.

(30) Foreign Application Priority Data

May 3, 2010 (EP) .................................... 10004640

(51) Int. Cl.
*A61B 5/117* (2016.01)
*A61B 5/1172* (2016.01)
*A61B 5/145* (2006.01)

(52) U.S. Cl.
CPC ........ *A61B 5/1172* (2013.01); *A61B 5/14532* (2013.01)

(58) Field of Classification Search
None
See application file for complete search history.

(56) References Cited

U.S. PATENT DOCUMENTS 7,009,497 B2 3/2006 Nicoletti et al.
7,116,805 B2 10/2006 Machida
(Continued)

FOREIGN PATENT DOCUMENTS

DE 10 2004 002 874 8/2005
JP 2006 109895 4/2006
(Continued)

*Primary Examiner* — P. Kathryn Wright
(74) *Attorney, Agent, or Firm* — Woodard, Emhardt, Moriarty, McNett & Henry LLP

(57) ABSTRACT

A measurement system and method for operating a measurement system is disclosed for an analyte determination. The system includes an analysis unit, which is configured to determine a measured analyte value for a body fluid specimen that is applied, a fingerprint sensor, which is configured to detect fingerprint sensor signals for one or various users, and a control unit, which is connected to the analysis unit and the fingerprint sensor unit for data transmission. The control unit is configured to perform a user identification using the detected fingerprint sensor signals and after successful user identification to enable a determination of a measured analyte value with the analysis unit for an identified user. The control unit is additionally configured to analyze the detected fingerprint sensor signals and optionally additional detected fingerprint sensor signals in addition to the user identification in order to provide control signals for performing additional measurement system functions.

24 Claims, 2 Drawing Sheets

(56) References Cited

U.S. PATENT DOCUMENTS

| | | |
|---|---|---|
| 2002/0009213 A1 | 1/2002 | Rowe et al. |
| 2002/0054695 A1 | 5/2002 | Bjorn et al. |
| 2003/0021452 A1* | 1/2003 | Hamid ............... G06K 9/00067 382/124 |
| 2004/0235192 A1 | 11/2004 | Guirguis |
| 2005/0169503 A1 | 8/2005 | Howell et al. |
| 2006/0089548 A1 | 4/2006 | Hogan |
| 2007/0016104 A1 | 1/2007 | Jansen et al. |
| 2007/0231209 A1 | 10/2007 | Cosentino et al. |
| 2008/0119710 A1 | 5/2008 | Reggiardo et al. |
| 2009/0010804 A1 | 1/2009 | Withrow, III et al. |
| 2009/0138207 A1 | 5/2009 | Cosentino et al. |
| 2011/0006880 A1 | 1/2011 | Long et al. |

FOREIGN PATENT DOCUMENTS

| | | |
|---|---|---|
| JP | 2007 193447 | 8/2007 |
| WO | WO 02/084605 A2 | 10/2002 |

* cited by examiner

MEASUREMENT SYSTEM FOR AN ANALYTE DETERMINATION AND A METHOD

CROSS-REFERENCE TO RELATED APPLICATION

The present application is a continuation of U.S. patent application Ser. No. 13/094,141 filed Apr. 26, 2011, which claims priority to European Patent Application No. 10004640.8 filed on May 3, 2010, which is incorporated herein by reference in its entirety.

FIELD OF THE INVENTION

The invention relates to a measurement system for an analyte determination, in particular for a blood glucose determination, as well as a method for operating a measurement system for the analyte determination.

BACKGROUND

Analyte measurement systems are intended to be used by one or more users to assay an analyte measured value, for example, the blood glucose value, based on analysis of a body fluid specimen, in particular a specimen of urine, saliva, serum, plasma or blood from the respective user. For this purpose, the measurement systems have an analysis device for experimentally analyzing the blood specimen to thereby ascertain a measured value for the blood glucose. The measurement systems usually have a control unit equipped with hardware and software components to control the operation of the measurement system, in particular also as a function of the detected inputs by the user who enters these values via one or more user interfaces of the measurement system. The measurement systems for the blood glucose assay are usually designed as handheld devices.

A portable glucose meter for assaying the blood glucose value of a blood specimen, which is configured for remote data transmission, is known from the document US 2009/0138207 A1. The known glucose meter has a patient identification unit, which may be designed with a biometric sensor, for example. A similar device is also described in the document US 2007/0231209 A1.

The document US 2009/0010804 A1 discloses an analysis device for analyzing a blood specimen, for example, which in one embodiment is provided with user identification based on fingerprint testing. A method of fingerprint verification is also known from the documents U.S. Pat. No. 7,116,805 and U.S. Pat. No. 7,009,497.

The document US 2007/0016104 A1 relates to a glucose meter, which in one embodiment performs a user identification with the help of analysis of a fingerprint. The glucose meter has an analysis device for analyzing blood specimens and a user identification method integrated into the analysis device. In operation of the glucose meter after successful user identification, operating parameters are adjusted according to the operating parameters allocated to the recognized user. The glucose meter may be used by multiple users, which is why it is a multi-user embodiment. By performing user identification, unauthorized persons are excluded from using the glucose meter.

SUMMARY

An improved measurement system is disclosed herein for analyte determination and a method for operating the measurement system, by which individual use of the measurement system is achieved by one or more persons and the efficiency thereof is improved, while operating convenience is optimized on the whole.

According to one aspect, a measurement system for analyte determination, in particular blood glucose determination, is disclosed that has an analysis device, which is configured to determine an analyte measured value, in particular a measured value for the blood glucose, for a given body fluid specimen, for example, a blood specimen, a fingerprint sensor device, which is configured to detect fingerprint sensor signals for one or multiple users, and a control device, which is connected to the analysis device for data transmission, and the fingerprint sensor device, such that the control device is configured to perform a user identification using the detected fingerprint sensor signals, and after successful user identification, to enable an assay of an analyte measured value using the analysis device for an identified user, and such that the control device is also configured to optionally also analyze additional detected fingerprint sensor signals in addition to the user identification in order to provide control signals for executing additional measurement system functions.

According to another aspect, a method for operating a measurement system for analyte determination, in particular for blood glucose determination is formed in a single or multi-user embodiment in which a fingerprint sensor device and an analysis device equipped for determination of an analyte measured value are connected to a control unit at least for data transmission, such that the method comprises the following steps: detection of fingerprint sensor signals by means of the fingerprint sensor unit, evaluating the detected fingerprint sensor signals by the control unit to identify a user, enabling an assay of an analyte measured value for a body fluid specimen to be fed into the unit using the analysis unit in successful user identification and providing control signals for execution of additional measurement system functions in that the detected fingerprint sensor signals and optionally other detected fingerprint sensor signals are additionally analyzed by means of the sensor unit in addition to the user identification.

The measurement systems and methods disclosed herein have the advantage in comparison with the prior art in that individualized use of the measurement system is made possible for the user in a simple and convenient manner, namely by touching the fingerprint sensor. In addition to the user identification that has been provided, the fingerprint sensor signals are analyzed by the control unit in order to be able to derive control signals, with which additional functions of the measurement system can be utilized. The fingerprint sensor signals are analyzed in a type of second use, i.e., in addition to their analysis in conjunction with the user identification. The supplementary analysis of the fingerprint sensor signals and providing the control signals are preferably performed after successful user identification independently of taking into account the electronic information. This may mean that the control signals are generated independently of user-specific information. Alternatively, it is also possible to provide for user-specific information to be taken into account in deriving the control signals in conjunction with the supplementary analysis of the fingerprint sensor signals, for example, with regard to special measurement system functions, which are stored or blocked in a retrievable manner by the control unit for a user in the measurement system.

In the supplementary analysis, the fingerprint sensor signals used for user identification may be analyzed entirely or partially. It may optionally be provided that additional fingerprint sensor signals are detected with the fingerprint sensor device.

One embodiment may provide that the measurement system is formed with a sample taking unit. One embodiment comprises a puncture unit for puncturing the skin for taking a blood specimen.

With the help of the user identification on the basis of the fingerprint sensor signals the measurement system can be designed as a multi-user embodiment.

According to another embodiment, the control unit is also configured to provide analyte measured values, in particular blood glucose values, which are determined with the help of the analysis unit for the body fluid specimen applied, in particular a blood specimen, after a successful user identification, data storage and/or output allocated to an identified user. The analyte measured values determined for an identified user are supplied for data storage and/or output in such a way that they are recognizably allocated to the identified user. For example, the data record allocated to a user is provided with an identifier which identifies the users. In conjunction with the data storage, it may be provided that a summary of memory areas assigned individually to different users is kept in the control unit. The analyte measured values assigned to an identified user are then stored in the respective memory area and can be read out there again.

In yet another embodiment, it is envisaged that the control unit is also configured to provide control signals for controlling a user menu and to control the user menu in accordance with the control signals in the supplementary analysis of the detected fingerprint sensor signals as a function of the detected fingerprint sensor signals. The user menu is displayed, for example, on a display screen integrated into the measurement system. The fingerprint sensor signals in this embodiment may be analyzed so that the user's navigation in the displayed user menu is detected. In one embodiment, the fingerprint sensor unit is therefore embodied as a type of trackball or trackpad device. In this way, it can also provide the user in particular with the option of defining operating parameters for operation of the measurement system in assay of the analyte measured value by means of the fingerprint sensor unit.

Another embodiment provides for the control unit to additionally be configured to identify a finger of a human hand in the supplementary analysis of the detected fingerprint sensor signals and to provide control signals assigned to this finger as a function of the identified finger. According to this embodiment, control signals assigned to the operating functions of the measurement system are generated as a function of the finger recognized. For example, it is possible to provide for the "ready-for-measurement mode" function to be triggered on recognition of the user's index finger. However, if the user's middle finger is detected, this means, for example, that the measurement system is blocked for further use so a mode such as "end of this use" is triggered. The measurement and the respective data storage are then terminated. Electronic information about the functions assigned to the various fingers is stored in the measurement system, so that the corresponding control signals can be generated on recognition of a certain finger of the hand. The finger-specific determination may be performed on a user-specific basis or independently of certain users.

According to a further embodiment, the control unit is also configured so that in the supplementary analysis of the detected fingerprint sensor signals, a finger tissue analysis is performed, and control signals for user information are provided as a function thereof.

In still a further embodiment, the measurement system further comprises an input unit configured to receive a code key, wherein the control unit is further configured to additionally analyze the received code key, to enable the determination of the analyte measured value and/or to provide the control signals for executing the additional measurement system functions. In this case a combined use of finger print identification and one or more code keys is possible. The code keys may also be referred to as security key in general. Such device is preferably used in a multi-mode or multi-role environment. For example, a physician must be authorized to access the system, he is then allowed to select a preinstalled protocol or mode of operation and give permission to a selected patient to collect data using this protocol. Thereby, steps of operation for reporting and using the results of the analysis of these data may be limited to the physician and the patient. As an option, after some anonymisation a meta-analysis may be allowed for a research person, or an overview analysis is done by a physician for all of his patients. In one embodiment, it is proposed to use a fingerprint sensor unit on a data collection device and rule sets in the software of the collection device and in an optional PC- or Server-Software useful to handle the collected date together with one or more code keys. Additional incorporation of a fingerprint sensor in an optional communication device used to ease data transfer and data management might give additional advantage. Such hardware configuration can be used in different use cases: on a single device a physician can log-in and then prepare this device for the patient; alternatively, a device used by the physician is coupled or paired with another device. This second device is then prepared to be handed over to the patient for data collection. The so-called physician device may be not a collection device, but may be a coupled communication device like a PC or a communication link device like Accu-Chek® S artPix, but it comprises a fingerprint sensor.

The code key based access method may be used to organize levels of access rights that are needed to organize such a multi-mode/multi-user system. In one embodiment, the system is opened up by a secure or code key, then the fingerprint sensor unit is activated. In all following occurrences of a needed key input, the fingerprint sensor unit is used instead of typing in a long code sequence.

In a multi-mode system there is a need for a whole set of "keys". The fingerprint signals of different fingers may be used to activate different modes of operation in the system. For example, after activating by input of a number code a physician scans his fingers, the image of the index finger will be used to pass on his activation to a patient for a special protocol. Thereby this patient receives rights to use the measurement device for this operation protocol. The physician can activate an editing function for protocols on the collection device, if he wants to change some conditions of a protocol to tailor it to a special patient, then his special protocol can be associated to a special patient.

In conjunction with the embodiments of the invention for operating a measurement system for determination of an analyte, in particular for a blood glucose determination, the explanations given in conjunction with the respective embodiments of the measurement system are applicable accordingly.

BRIEF DESCRIPTION OF THE DRAWINGS

The invention is explained in greater detail below on the basis of exemplary embodiments with reference to the figures.

DETAILED DESCRIPTION

Figure 1:
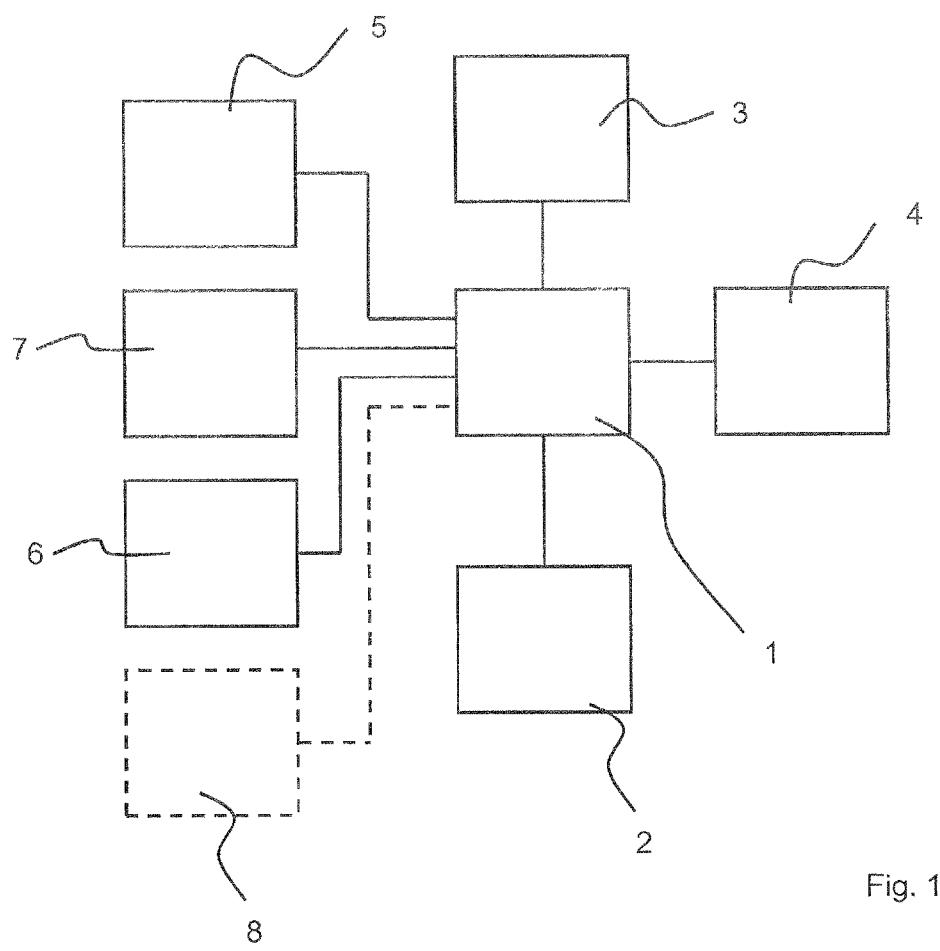
FIG. 1 is a schematic diagram of a measurement system for analyte determination in a multi-user embodiment.

For the purposes of promoting an understanding of the principles of the invention, reference will now be made to the embodiments illustrated in the drawings and specific language will be used to describe the same. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

Although an exemplary embodiment is described below on the basis of a measurement system for blood glucose determinations from blood specimens, the invention is not limited to this. The proposed technologies may also be used for other substances and parameters to be detected and for other specimen fluids such as serum, plasma, urine, saliva or the like, which are referred to jointly here as "analytes". Additional analytes in the sense understood here include not only glucose but also in particular lactate, cholesterol, triglycerides, coagulation parameters, such as the prothrombin time (Quick value) and the like.

The measurement system may connect to a server device from which electronic data may be received. The electronic data may belong to any operation aspect of the measurement device. Different sets of electronic data received from the server device may be applied depending on the result of key and/or finger print analysis.

FIG. 1 shows a schematic diagram of a measurement system for blood glucose determination in a multi-user embodiment, i.e., in a device embodiment, allowing use by one person or preferably multiple different persons. The measurement system is therefore equipped with hardware and software components as explained in more detail below.

In this measurement system, a control unit 1 is connected to an analysis unit 2 for data transmission. With the help of the analysis unit 2, a specimen of blood taken from a user can be analyzed with regard to the blood glucose value in particular. Such a use of the measurement system by one or more users is possible only if the user is first recognized as part of a user identification. For the user identification, the measurement system has a fingerprint sensor unit 3 coupled to the control unit I. Each user is identified by placing one or more fingers on the fingerprint sensor unit 3. The identification is successful if, on the basis of electronic data stored in the measurement system on the one hand and the analysis of the detected fingerprint sensor signals on the other hand, the control until 1 ascertains that the fingerprint sensor signals can be assigned to an authorized user. After successful user identification in this way, the measurement system is released for analysis of a blood specimen by analysis unit 2.

The blood glucose values determined as part of the analysis are stored in a memory unit 4 in a user-allocated manner and/or are made available for data output via a data output interface 5, whether for a hardwired data output or a wireless data output. In addition or alternatively, the measured values may be displayed on a display 6. The blood glucose values determined are assigned to the identified user, for example, by providing an identifier for the user to accompany the data record with the measured values for the blood glucose.

In the embodiment shown in FIG. 1, the measurement system also has a sample taking unit 7, which is configured to enable the user to obtain a blood specimen after successful user identification. The blood specimen taken is then transferred to the analysis unit 2 and analyzed there along a capillary system, for example.

If another embodiment involves a measurement system for determining another analyte in a body fluid specimen, then the analysis unit 2 and the sample taking unit 7 in particular are designed accordingly. Analysis units and sample taking units are known as such in various embodiments, therefore no further explanation is required here.

The measurement system may optionally have one or more additional device components 8, which is indicated by dashed lines in FIG. 1. For example, an input unit may be provided, the input unit being configured to receive one or more code keys. In a preferred embodiment, the code key is received in response to a user input.

The control unit 1 is also configured to analyze the detected fingerprint sensor signals via the fingerprint sensor device 3 beyond user identification to supply control signals for other operating functions of the measurement system. This includes, for example, deriving control signals for a user interface formed with the display 6 and coupled to the control unit 1 for data transmission. For example, the user can in this way navigate in a graphical user menu and may select functionalities by means of the fingerprint sensor unit 3. In this case, the fingerprint sensor unit 3 is embodied as a type of trackpad device, for example.

Alternatively or additionally, the further analysis of the fingerprint sensor signals with the help of the control unit 1 may provide that control signals are generated as a function of the type of finger recognized so that, for example, first control signals are generated when the index finger is recognized, whereas second control signals are supplied when another finger on the user's hand is recognized in a supplementary analysis of the fingerprint sensor signals. In this case, the control unit 1 has electronic information, which is assigned certain operating functions of the measurement system as a function of the type of finger. Therefore, electronic information for an assignment between the type of finger on the one hand and the operating functionality of the measurement system on the other hand is stored in memory unit 4, for example.

As an alternative or in addition, code key analysis may be used for identifying different users and/or modes of operation assigned to different users. For example, first a master user, e.g. a physician, may be identified by the finger print sensor device 3. After identification of the master user the measurement system is cleared for operation in general. Following, a specific user may identify itself by a code key. Code key identification may clear the measurement device for the determination of a certain analyte.

In additional or alternatively, the control unit 1 is configured to perform a finger tissue analysis in the more extensive analysis of the detected fingerprint sensor signals and to derive control signals as a function thereof for the measurement system. Thus the supplementary analysis of the fingerprint sensor signals may reveal extensive scarring of the tissue of the finger for which the sensor signals have been detected, which may be the result of frequent blood sampling on this finger. If in the supplementary analysis of the fingerprint sensor signals, such a circumstance is recognized by the control unit, control signals are generated, notifying the user by way of the display 6 that it is advisable to take the blood specimen from another finger. Supplementary or alternative optical signaling in the form of a colored lamp may also be provided, depending on the result of the finger tissue analysis. Thus, a red control display could signal to the user of the measurement system that the finger initially placed on the fingerprint sensor unit 3 is not suitable for taking a blood specimen.

Figure 2:
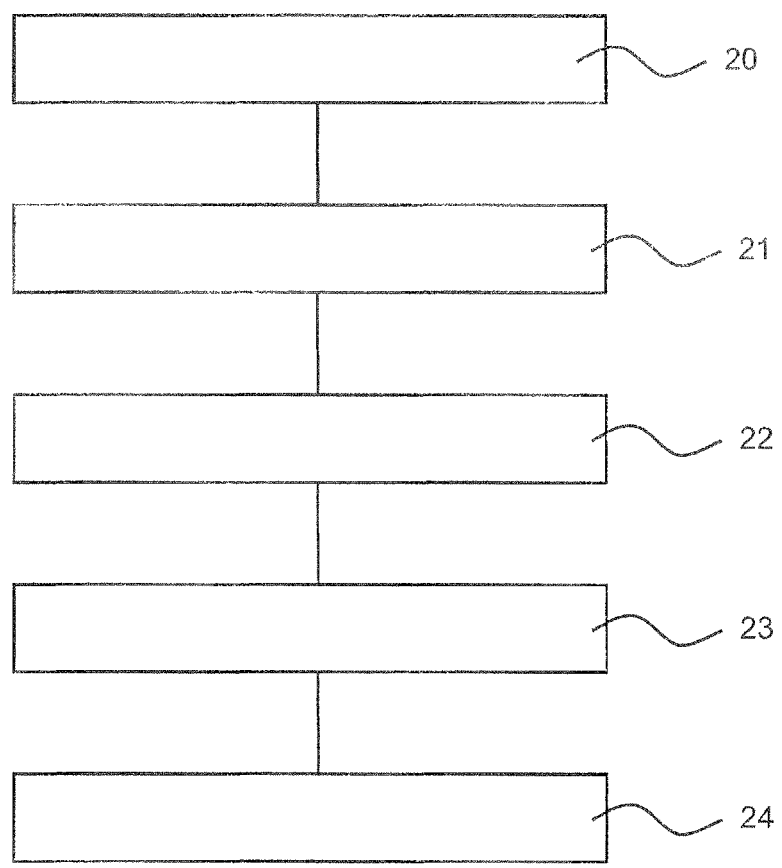
FIG. 2 shows schematically a sequence in operation of the measurement system from FIG. 1.

In summary, FIG. 2 shows a flowchart for operation of the measurement system from FIG. 1 in an exemplary embodiment. First, user identification is performed in a step 20. If user identification is successful, then in step 21 the measurement system is enabled for use by the identified user. Then in step 22 the detected fingerprint sensor signals and/or optionally any fingerprint sensor signals additionally detected beyond the user identification are analyzed to derive control signals for additional measurement system functions. This may be done before, during and/or after blood specimen has been analyzed. According to FIG. 2, a blood specimen is then analyzed in step 23 in the selected exemplary embodiment. Next in step 24, the measured blood glucose values thereby obtained are supplied for data storage and/or they are output in correlation with the identified user.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A measurement system for analyte determination, comprising:
   a display screen;
   an analysis unit, which is configured to determine an analyte measured value for a body fluid specimen applied,
   a fingerprint sensor unit, which is configured to detect fingerprint sensor signals for one or various users, and
   a control unit, which is connected to the analysis unit and to the fingerprint sensor unit for data transmission,
   wherein the control unit is configured to perform a user identification using fingerprint sensor signals detected and to enable a determination of an analyte measured value on successful user identification using the analysis unit for an identified user, and
   wherein, in addition to the user identification, the control unit is additionally configured to perform a finger tissue analysis in a supplementary analysis of the detected fingerprint sensor signals, and to provide control signals for user information as a function thereof the control signals displaying on the display screen a notification to the user comprising at least one of a notification that the finger placed on the fingerprint sensor unit is not suitable for taking a blood sample and a notification to the user to take the blood sample from another finger based on the finger tissue analysis.

2. The measurement system according to claim 1, wherein the control unit is additionally configured to provide, on successful user identification, analyte measured values which are determined with the help of the analysis unit for the body fluid specimen applied, assigned to the identified user for at least one of data storage and output.

3. The measurement system according to claim 1, wherein the control unit is additionally configured to provide control signals for controlling a user menu in a second supplementary analysis of the fingerprint sensor signals detected as a function of the fingerprint sensor signals detected for controlling a user menu and to control the user menu in accordance with the control signals.

4. The measurement system according to claim 3, wherein the control unit is additionally configured to identify a finger of a human hand in the second supplementary analysis of the detected fingerprint sensor signals and to provide control signals assigned to this finger as a function of the finger identified.

5. The measurement system according to claim 1, further comprising an input unit configured to receive a code key, wherein the control unit is further configured to additionally analyze the received code key, to enable the determination of the analyte measured value and to provide the control signals for executing the additional measurement system functions.

6. The measurement system according to claim 1, further comprising an input unit configured to receive a code key, wherein the control unit is further configured to additionally analyze the received code key, to enable the determination of the analyte measured value.

7. The measurement system according to claim 1, further comprising an input unit configured to receive a code key, wherein the control unit is further configured to additionally analyze the received code key, to provide the control signals for executing the additional measurement system functions.

8. The measurement system according to claim 1, wherein the control unit is additionally configured to detect scarring of the finger tissue from the finger tissue analysis, the control signals displaying a notification to the user based on the detecting of scarring.

9. The measurement system according to claim 1 in which the notification to the user is to take the blood sample from another finger.

10. The measurement system according to claim 9 in which the notification to the user to take the blood sample from another finger is based upon detecting scarring of the finger tissue.

11. The measurement system according to claim 1 in which the notification to the user is that the finger is not suitable for taking a blood specimen.

12. The measurement system according to claim 11 in which the notification that the finger is not suitable for taking a blood specimen is based upon detecting scarring of the finger tissue.

13. A method for operating a measurement system for analyte determination, in which a fingerprint sensor unit and an analysis unit equipped for determination of an analyte measured value are connected to a control unit at least for data transmission and a display screen, such that the method comprises the following steps:
   detecting fingerprint sensor signals by means of the fingerprint sensor unit,
   analyzing the detected fingerprint sensor signals by means of the control unit to identify a user,
   enabling a determination of an analyte measured value for a body fluid specimen to be applied with the analysis unit after successful user identification, and
   providing control signals for performing additional measurement systems functions by analyzing the detected fingerprint sensor signals by means of the control unit in addition to the user identification,
   wherein a finger tissue analysis is performed in a supplementary analysis of the detected fingerprint sensor signals, and control signals for user information are supplied as a function thereof, the control signals including displaying on the display screen a notification to the user comprising at least one of a notification that the finger placed on the fingerprint sensor unit is not suitable for taking a blood sample and a notification to the user to take the blood sample from another finger based on the finger tissue analysis.

14. The method according to claim 13, wherein after successful user identification, analyte measured values which have previously been determined with the help of the analysis unit for a body fluid specimen applied are supplied for at least one of data storage and output in allocation to the identified user by means of the control unit.

15. The method according to claim 13, wherein control signals are made available for controlling a user menu in a second supplementary analysis of the detected fingerprint sensor signals as a function of the detected fingerprint sensor signals, and the user menu is controlled according to the control signals.

16. The method according to claim 15, wherein one or more fingers of a human hand are identified in the second supplementary analysis of the detected fingerprint sensor signals, and control signals are supplied as a function of the finger or all the identified fingers.

17. The method according to claim 13, wherein a code key is received by an input unit and the control unit additionally analyzes the received code key for enabling the determination of the analyte measured value and providing the control signals for executing the additional measurement system functions.

18. The method according to claim 13, wherein a code key is received by an input unit and the control unit additionally analyzes the received code key for enabling the determination of the analyte measured value.

19. The method according to claim 13, wherein a code key is received by an input unit and the control unit additionally analyzes the received code key for providing the control signals for executing the additional measurement system functions.

20. The method according to claim 13, wherein the supplementary analysis of the detected fingerprint sensor signals is to detect scarring of the finger tissue from the finger tissue analysis, the control signals displaying a notification to the user based on the detecting of scarring.

21. The method according to claim 13 in which the providing control signals comprises displaying the notification to the user to take the blood sample from another finger.

22. The method according to claim 21 in which the displaying the notification to the user to take the blood sample from another finger is based upon detecting scarring of the finger tissue.

23. The method according to claim 13 in which the providing control signals comprises displaying the notification to the user that the finger is not suitable for taking a blood specimen.

24. The method according to claim 23 in which the displaying the notification to the user that the finger is not suitable for taking a blood sample is based upon detecting scarring of the finger tissue.

* * * * *